United States Patent
Will et al.

(10) Patent No.: US 8,658,366 B2
(45) Date of Patent: Feb. 25, 2014

(54) DETECTION OF TARGET VARIANTS USING A FLUORESCENT LABEL AND A SOLUBLE QUENCHER

(75) Inventors: Stephen Gordon Will, Oakland, CA (US); Amar P. Gupta, Danville, CA (US); Laura Geyer, Hercules, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 373 days.

(21) Appl. No.: 12/559,296

(22) Filed: Sep. 14, 2009

(65) Prior Publication Data

US 2010/0124744 A1    May 20, 2010

Related U.S. Application Data

(60) Provisional application No. 61/098,186, filed on Sep. 18, 2008.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
None
See application file for complete search history.

(56) References Cited

U.S. PATENT DOCUMENTS

| 2007/0020664 A1 | 1/2007 | Gupta et al. |
| 2007/0020665 A1* | 1/2007 | Gupta et al. ..................... 435/6 |
| 2007/0172836 A1 | 7/2007 | Exner et al. |

FOREIGN PATENT DOCUMENTS

| WO | WO 01/11078 A1 | 2/2001 |
| WO | WO 02/097132 A1 | 12/2002 |
| WO | WO 2004/033726 A1 | 4/2004 |
| WO | WO 2007/093816 A1 | 8/2007 |

OTHER PUBLICATIONS

Gundry et al. Amplicon melting analysis with labeled primers: a closed-tube method for differentiating homozygotes and heterozygotes. Clinical Chem. (2003) vol. 49, No. 3, pp. 396-406.*
Gingeras, Thomas R. et al.; "Fifty Years of Molecular (DNA/RNA) Diagnostics"; 2005, *Clinical Chemistry*, vol. 51, No. 3, pp. 1-11.
Howell, W. Mathias et al.; "iFRET: An Improved Fluorescence System for DNA-Melting Analysis"; 2002, *Genome Research*, vol. 12, pp. 1401-1407.

* cited by examiner

*Primary Examiner* — Kenneth R. Horlick
*Assistant Examiner* — David Thomas
(74) *Attorney, Agent, or Firm* — Kilpatrick Townsend & Stockton LLP

(57) ABSTRACT

Methods, reaction mixtures and systems for detecting the presence or absence of a target nucleic acid variant from a selection of possible variants is described.

12 Claims, 2 Drawing Sheets

DETECTION OF TARGET VARIANTS USING A FLUORESCENT LABEL AND A SOLUBLE QUENCHER

CROSS-REFERENCES TO RELATED APPLICATIONS

The present application claims benefit of priority to U.S. Provisional Patent Application No. 61/098,186, filed Sep. 18, 2008, which is incorporated by reference for all purposes. All of the following patent applications are incorporated by reference in their entirety: U.S. patent application Ser. No. 11/474,062, and U.S. patent application Ser. No. 11/474,125, each filed on filed Jun. 23, 2006, and each of which claims benefit of priority to U.S. Provisional Patent Application No. 60/695,991, filed Jun. 30, 2005; U.S. Provisional Patent Application No. 60/696,253, filed Jun. 30, 2005; U.S. Provisional Patent Application No. 60/696,293, filed Jun. 30, 2005; and U.S. Provisional Patent Application No. 60/696,303, filed Jun. 30, 2005.

BACKGROUND OF THE INVENTION

The development of nucleic acid amplification technology has revolutionized genetic analysis and engineering science. For example, the polymerase chain reaction (PCR) is commonly utilized to amplify specific target nucleic acids using selected primer nucleic acids, e.g., to facilitate the detection of the target nucleic acid as part of a diagnostic, forensic, or other application. Primers typically function in pairs that are designed for extension towards each other to cover the selected target region. A typical PCR cycle includes a high temperature (e.g., 85° C. or more) denaturation step during which the strands of double-stranded nucleic acids separate from one another, a low temperature (e.g., 45-65° C.) annealing step during which the primers hybridize to the separated single strands, and an intermediate temperature (e.g., around 72° C.) extension step during which a nucleic acid polymerase extends the primers. Two-temperature thermocycling procedures are also utilized. These generally include a high temperature denaturation step and a low temperature anneal-extend step.

PCRs are also described in many different U.S. patents including, e.g., U.S. Pat. No. 4,683,195, entitled "PROCESS FOR AMPLIFYING, DETECTING, AND/OR-CLONING NUCLEIC ACID SEQUENCES," which issued to Mullis et al. Jul. 28, 1987, U.S. Pat. No. 4,683,202, entitled "PROCESS FOR AMPLIFYING NUCLEIC ACID SEQUENCES," which issued to Mullis Jul. 28, 1987, and U.S. Pat. No. 4,965,188, entitled "PROCESS FOR AMPLIFYING, DETECTING, AND/OR CLONING NUCLEIC ACID SEQUENCES USING A THERMOSTABLE ENZYME," which issued to Mullis et al. Oct. 23, 1990, which are each incorporated by reference. Further, PCR-related techniques are also described in various other publications, such as Innis et al. (Eds.) *PCR Protocols: A Guide to Methods and Applications*, Elsevier Science & Technology Books (1990), Innis et al. (Eds.) *PCR Applications: Protocols for Functional Genomics*, Academic Press (1999), Edwards et al., *Real-Time PCR*, Taylor & Francis, Inc. (2004), and Rapley et al., *Molecular Analysis and Genome Discovery*, John Wiley & Sons, Inc. (2004), which are each incorporated by reference.

Many variations of the PCR as well as other nucleic acid amplification techniques have also been developed. Examples of these include reverse-transcription PCR (RT-PCR) (Joyce (2002) "Quantitative RT-PCR. A review of current methodologies" *Methods Mol. Biol.* 193:83-92 and Emrich et al. (2002) "Quantitative detection of telomerase components by real-time, online RT-PCR analysis with the LightCycler," Methods Mol. Biol. 191:99-108), the ligase chain reaction (LCR) (Lee (1996) "Ligase chain reaction," *Biologicals* 24(3):197-9), the polymerase ligase chain reaction (Barany et al. (1991) "The ligase chain reaction in a PCR world," *PCR Methods Appl.* 1(1):5-16), the Gap-LCR (Abravaya et al. (1995) "Detection of point mutations with a modified ligase chain reaction (Gap-LCR)," *Nucleic Acids Res.* 23(4):675-82), strand displacement amplification (Walker (1993) "Empirical aspects of strand displacement amplification," *PCR Methods Appl.* 3(1):1-6), linked linear amplification (LLA) (Killeen et al. (2003) "Linked linear amplification for simultaneous analysis of the two most common hemochromatosis mutations," *Clin Chem.* 49(7):1050-7), rolling circle amplification (RCA) (Nilsson et al. (2002) "Real-time monitoring of rolling-circle amplification using a modified molecular beacon design," *Nucleic Acids Res.* 30(14):e66), transcription-mediated amplification (TMA) (Emery et al. (2000) "Evaluation of performance of the Gen-Probe human immunodeficiency virus type 1 viral load assay using primary subtype A, C, and D isolates from Kenya," *J Clin Microbiol* 38:2688-2695), nucleic-acid-sequence-based amplification (NASBA) (Mani et al. (1999) "Plasma RNA viral load as measured by the branched DNA and nucleic acid sequence-based amplification assays of HIV-1," *J Acquir Immune Defic Syndr* 22:208-209 and Berndt et al. (2000) "Comparison between a nucleic acid sequence-based amplification and branched DNA test for quantifying HIV RNA load in blood plasma," *J Virol Methods* 89:177-181), and self-sustaining sequence replication (3SR) (Mueller et al. (1997) "Self-sustained sequence replication (3SR): an alternative to PCR," *Histochem Cell Biol* 108:431-7), which are each incorporated by reference.

Various strategies for detecting amplification products have been developed, including those involving 5' nuclease probes, molecular beacons, or SCORPION® primers, among many others. To illustrate, a 5' nuclease assay typically utilizes the 5' to 3' nuclease activity of certain DNA polymerases to cleave 5' nuclease probes during the course of a polymerase chain reaction (PCR). These assays allow for both the amplification of a target and the release of labels for detection, generally without resort to multiple handling steps of amplified products. Certain 5' nuclease probes include labeling moieties, such as a fluorescent reporter dye and a quencher dye. When the probe is intact, the proximity of the reporter dye to the quencher dye generally results in the suppression of the reporter fluorescence. In many cases, however, an intact probe produces a certain amount of residual or baseline fluorescence. During a 5' nuclease reaction, cleavage of the probe separates the reporter dye and the quencher dye from one another, resulting in a detectable increase in fluorescence from the reporter. The accumulation of PCR products or amplicons is typically detected indirectly by monitoring this increase in fluorescence in real-time.

BRIEF SUMMARY OF THE INVENTION

The present invention provides for methods of detecting the presence or absence of a target nucleic acid variant in a sample, wherein a target nucleic acid may occur in at least two variants. In some embodiments, the method comprises (a) providing at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;
(b) providing at least one soluble light emission modifier, which, when the modifier non-covalently binds double stranded DNA incorporating the labeled oligonucleotide, alters light emission from the first label compared to light emission of the first label in the presence of the soluble light emission modifier when the labeled oligonucleotide is single-stranded;
(c) amplifying the target nucleic acid in the sample in the presence of the labeled oligonucleotide and the soluble light emission modifier in an amplification reaction under the selected condition such that the labeled oligonucleotide is extended to produce at least a first labeled amplicon (or if more than one variant of the template is present, 2, 3, or more different labeled amplicons) incorporating the labeled oligonucleotide, wherein the first labeled amplicon has a different melting temperature depending on which of the at least two target nucleic variants are amplified;
(d) detecting the melting temperature of the amplicon by monitoring the signal of the label under changing temperature; and
(e) correlating the melting temperature to the presence of one of the at least two target variants, thereby detecting the presence or absence of a target nucleic acid variant in a sample.

In some embodiments, the method further comprises providing a second labeled oligonucleotide comprising a second label, which second label comprises at least one light emitting moiety and wherein at least a subsequence of the second labeled oligonucleotide is sufficiently complementary to at least a second subsequence of the target nucleic acid that may occur in at least two variants such that the second labeled oligonucleotide hybridizes with the second target nucleic acid under the selected condition, and wherein signal from the second label can be distinguished from the signal of the first label,
wherein the at least one soluble light emission modifier, when intercalated in double stranded DNA incorporating the second labeled oligonucleotide alters light emission from the second label compared to light emission of the second label when the second labeled oligonucleotide is single-stranded in the presence of the soluble light emission modifier;
wherein the sample comprises at least one (and optionally 2, 3, or more) variant(s) of the target nucleic acid and the amplifying step (c) further comprises amplifying the nucleic acid in the sample in the presence of the second labeled oligonucleotide in the amplification reaction such that the second labeled oligonucleotide is extended to produce a second labeled amplicon (or if more than one variant of the template is present, 2, 3, or more different labeled amplicons) incorporating the second labeled oligonucleotide, and wherein the second labeled amplicon has a different melting temperature depending on which of the at least two target nucleic acid variants are amplified;
wherein the detecting step (d) further comprises detecting the melting temperature of the second labeled amplicon by monitoring the signal of the second label under changing temperature; and
wherein the correlating step (e) further comprises correlating the melting temperature of the second labeled amplicon to the presence of a second target nucleic acid variant.

In some embodiments, the method further comprises providing a third labeled oligonucleotide comprising a third label, which third label comprises at least one light emitting moiety and wherein at least a subsequence of the third labeled oligonucleotide is sufficiently complementary to at least a third subsequence of the target nucleic acid that may occur in at least two variants such that the third labeled oligonucleotide hybridizes with the third target nucleic acid under the selected condition, and wherein signal from the third label can be distinguished from the signal of the first and second label,
wherein the at least one soluble light emission modifier, when intercalated in double stranded DNA incorporating the third labeled oligonucleotide alters light emission from the third label compared to light emission of the third label when the third labeled oligonucleotide is single-stranded in the presence of the soluble light emission modifier;
wherein the sample comprises at least one (and optionally 2, 3, or more) variant(s) of the target nucleic acid and the amplifying step (c) further comprises amplifying the nucleic acid in the sample in the presence of the third labeled oligonucleotide in the amplification reaction such that the third labeled oligonucleotide is extended to produce a third labeled amplicon (or if more than one variant of the template is present, 2, 3, or more different labeled amplicons) incorporating the third labeled oligonucleotide, and wherein the third labeled amplicon has a different melting temperature depending on which of the at least two target nucleic acid variants are amplified;
wherein the detecting step (d) further comprises detecting the melting temperature of the third labeled amplicon by monitoring the signal of the third label under changing temperature; and
wherein the correlating step (e) further comprises correlating the melting temperature of the third labeled amplicon to the presence of a third target nucleic acid variant.

In some embodiments, the second labeled amplicon comprises different target nucleic acid variant sequences compared to the first labeled amplicon.

In some embodiments, the modifier is a diazine dye or a thiazine dye.

In some embodiments, the modifier is selected from the group consisting of an azocarmine dye, a phenazine dye, an oxazine dye, diethylsafraninazodimethylaniline chloride, methylene blue, methylene green, thionin, 1,9-dimethylmethylene blue, sym-dimethylthionin, toluidine blue O, new methylene blue, methylene violet bernthsen, azure A, azure B, and azure C.

In some embodiments, the first label comprises a fluorescent dye.

In some embodiments, the first label is selected from the group consisting of a rhodamine dye, flourescein dye, and a cyanine dye.

In some embodiments, the second label is selected from the group consisting of a rhodamine dye, flourescein dye, and a cyanine dye.

In some embodiments, the target nucleic acid is a pathogen nucleic acid.

In some embodiments, the target nucleic acid is a viral nucleic acid.

In some embodiments, the melting temperatures of the amplicons of the at least two variants differ by at least 5 degrees C.

The present invention also provides reaction mixture as described herein. In some embodiments, the reaction mixture comprises:
a target nucleic acid;
at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;

at least one soluble light emission modifier, which, when the modifier binds double stranded DNA incorporating the labeled oligonucleotide, alters light emission from the first label compared to light emission of the first label in the presence of the soluble light emission modifier when the labeled oligonucleotide is single-stranded;
wherein all of the oligonucleotides less than 100 nucleotides in length are labeled.

The present invention also provides reaction mixtures comprising:
a target nucleic acid;
at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;
at least one soluble light emission modifier, which, when the modifier binds double stranded DNA incorporating the labeled oligonucleotide, alters light emission from the first label compared to light emission of the first label in the presence of the soluble light emission modifier when the labeled oligonucleotide is single-stranded; and
a single or double-stranded second amplicon polynucleotide (or if more than one variant of the template is present, 2, 3, or more different labeled amplicons), wherein the first amplicon polynucleotide comprises the label and the sequence of the labeled oligonucleotide.

In some embodiments, all of the oligonucleotides are labeled.

In some embodiments, the first label comprises a fluorescent dye.

In some embodiments, the reaction mixture further comprises one or more of: a buffer, a salt, a metal ion, a nucleotide incorporating biocatalyst, or a deoxynucleotide.

In some embodiments, the modifier is a diazine dye or a thiazine dye.

In some embodiments, the modifier is selected from the group consisting of an azocarmine dye, a phenazine dye, an oxazine dye, diethylsafraninazodimethylaniline chloride, methylene blue, methylene green, thionin, 1,9-dimethylmethylene blue, sym-dimethylthionin, toluidine blue O, new methylene blue, methylene violet bernthsen, azure A, azure B, and azure C.

In some embodiments, the first label is selected from the group consisting of a rhodamine dye, flourescein dye, and a cyanine dye.

In some embodiments, the target nucleic acid is a pathogen nucleic acid.

In some embodiments, the target nucleic acid is a viral nucleic acid.

In some embodiments, the reaction mixture further comprises
a second labeled oligonucleotide comprising a second label, which second label comprises at least one light emitting moiety and wherein at least a subsequence of the second labeled oligonucleotide is sufficiently complementary to at least a second subsequence of the target nucleic acid that may occur in at least two variants such that the second labeled oligonucleotide hybridizes with the second target nucleic acid under the selected condition, and wherein signal from the second label can be distinguished from the signal of the first label,
wherein the at least one soluble light emission modifier, when intercalated in double stranded DNA incorporating the second labeled oligonucleotide alters light emission from the second label compared to light emission of the second label when the second labeled oligonucleotide is single-stranded in the presence of the soluble light emission modifier.

In some embodiments, the reaction mixture further comprising
a second labeled oligonucleotide comprising a second label, which second label comprises at least one light emitting moiety and wherein at least a subsequence of the second labeled oligonucleotide is sufficiently complementary to at least a second subsequence of the target nucleic acid that may occur in at least two variants such that the second labeled oligonucleotide hybridizes with the second target nucleic acid under the selected condition, and wherein signal from the second label can be distinguished from the signal of the first label,
wherein the at least one soluble light emission modifier, when intercalated in double stranded DNA incorporating the second labeled oligonucleotide alters light emission from the second label compared to light emission of the second label when the second labeled oligonucleotide is single-stranded in the presence of the soluble light emission modifier; and
a single or double-stranded second amplicon polynucleotide (or if more than one variant of the template is present, 2, 3, or more different labeled amplicons), wherein the first amplicon polynucleotide comprises the label and the sequence of the second labeled oligonucleotide.

It will be appreciated that a third, fourth, fifth, etc. labeled oligonucleotide/labeled amplicon can also be present depending on the number of labeled oligonucleotides required or desired and depending on the presence or absence of the appropriate template.

DEFINITIONS

Figure 1:
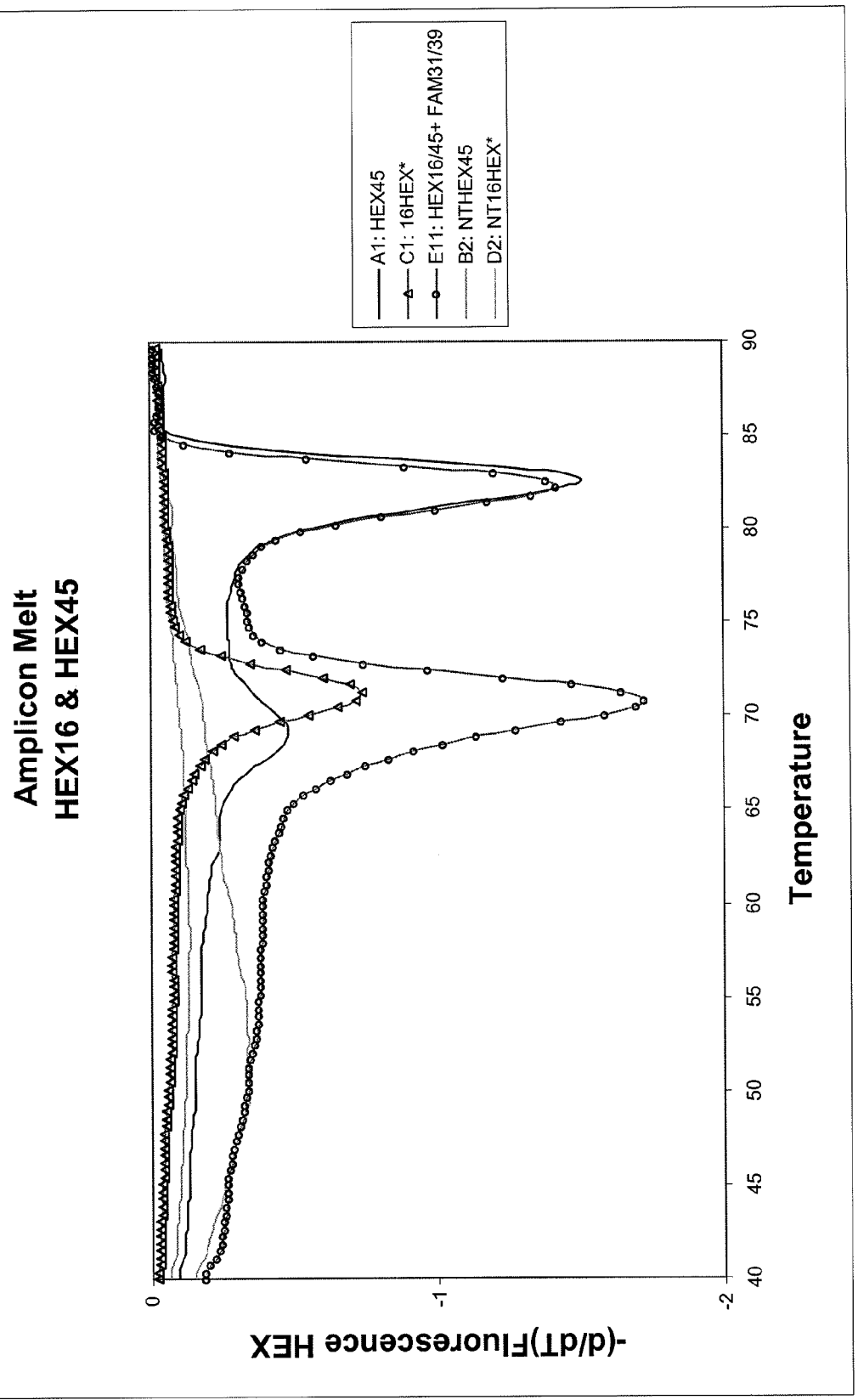
FIG. 1 illustrates melt curves of amplicons generated using HPV16 primers on an HPV16 template, HPV45 primers on a HPV45 template, or mixtures of both sets of primers and templates.

An "amplicon" refers to a molecule made by amplifying a nucleic acid molecule, e.g., as occurs in a nucleic acid amplification reaction, such as a polymerase chain reaction ("PCR"), a strand displacement amplification (SDA), transcription mediated amplification (TMA), ligase chain reaction (LCR), or other nucleic acid amplification technique. Typically, an amplicon is a copy of a selected nucleic acid (e.g., a template or target nucleic acid), a portion thereof (e.g., at least 50, 100, 200, 500, 1000 base pairs or more of a target nucleic acid) or is complementary thereto.

An "amplification reaction" refers to a reaction involving the replication of one or more target nucleic acid sequences or complements thereto. Exemplary amplification reactions include PCR, ligase chain reactions (LCR), among many others.

A "complement" of a nucleic acid refers to a nucleic acid segment that can combine in an antiparallel association or hybridize with at least a subsequence of that nucleic acid, for example as "Watson-Crick base pairs." The antiparallel association can be intramolecular, e.g., in the form of a hairpin loop within a nucleic acid, or intermolecular, such as when two or more single-stranded nucleic acids hydrize with one another. Certain bases not commonly found in natural nucleic acids may be included in the nucleic acids referred to herein and include, for example, inosine, 7-deazaguanine and those discussed below. Complementarity need not be perfect; stable duplexes of polynucleotides, for example, may contain mismatched base pairs or unmatched bases such that there are complementary and non-complementary regions. Those skilled in the art of nucleic acid technology can determine duplex stability by empirically considering a number of variables including, for example, the length of a region of complementarity, base composition and sequence of nucleotides in a region of complementarity, ionic strength, and incidence of mismatched base pairs.

A "diazine dye" refers to any of a class of organic chemical compounds containing a benzene ring in which two of the carbon atoms have been replaced by nitrogen atoms. Exemplary diazine dyes include an azocarmine dye, a phenazine dye, an oxazine dye, and diethylsafraninazodimethylaniline chloride (Janus Green B or Diazine Green 5).

Nucleic acids "hybridize" when complementary single strands of nucleic acid pair to give a double-stranded nucleic acid sequence. Hybridization occurs due to a variety of well-characterized forces, including hydrogen bonding, solvent exclusion, and base stacking. An extensive guide to nucleic hybridization may be found in Tijssen, *Laboratory Techniques in Biochemistry and Molecular Biology—Hybridization with Nucleic Acid Probes*, part I, chapter 2, "Overview of principles of hybridization and the strategy of nucleic acid probe assays," Elsevier (1993).

A "label" or "labeling moiety" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like. To further illustrate, fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include, e.g., Texas Red, ROX, R110, R6G, and TAMRA. FAM, HEX, TET, JOE, NAN, ZOE, ROX, R110, R6G, and TAMRA are commercially available from, e.g., Perkin-Elmer, Inc. (Wellesley, Mass., USA), and Texas Red is commercially available from, e.g., Molecular Probes, Inc. (Eugene, Oreg.). Dyes of the cyanine family include, e.g., Cy2, Cy3, Cy5, and Cy7, and are commercially available from, e.g., Amersham Biosciences Corp. (Piscataway, N.J., USA). Additional labels are referred to herein or are otherwise known in the art.

A "light emission modifier" refers to a substance that non-covalently associates (e.g., non-covalently binds, for example to the minor or major groove, intercalates, adsorbs, etc.) with a nucleic acid in a mixture and that changes the detectable emission of radiation from a radiation source (e.g., a fluorescent moiety) associated with the nucleic acid when the substance is proximal to the radiation source. In some embodiments, for example, certain light emission modifiers described herein reduce or quench the emission of light that would otherwise be emitted (e.g., a baseline emission of light) from oligonucleotides that include at least one light-emitting moiety (e.g., primers) when the light emission modifiers are contacted with those oligonucleotides. Light emission modifiers are typically soluble and in these embodiments are also referred to as "soluble quenchers" or "soluble light emission modifiers". In addition, without being bound by any particular theory, it is believed that a light emission modifier generally binds to nucleic acids in a length dependent manner and bind much more strongly to double stranded nucleic acids compared to single stranded nucleic acids. That is, light emission modifiers typically bind to longer nucleic acids to a greater extent than to relatively shorter nucleic acids. Accordingly, the extent to which a light emission modifier modifies the emission of light from a given labeled nucleic acid will depend on whether the labeled nucleic acid is single- or double-stranded. Exemplary light emission modifiers include various diazine and thiazines dyes, which are described further herein.

A "light-emitting labeling moiety" refers to a labeling moiety that generates or is capable of generating detectable radiation or light. Certain light-emitting labeling moieties generate light, e.g., by fluorescence, chemiluminescence, bioluminescence, or the like.

A "mixture" refers to a combination of two or more different components. A "reaction mixture" refers a mixture that comprises molecules that can participate in and/or facilitate a given reaction. To illustrate, an amplification reaction mixture generally includes a solution containing reagents necessary to carry out an amplification reaction, and typically contains primers, a nucleic acid polymerase, dNTPs, and a divalent metal cation in a suitable buffer. A reaction mixture is referred to as "complete" if it contains all reagents necessary to carry out the reaction, and "incomplete" if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Reaction components may also be formulated in a dry form, e.g., tablets, and may then be reconstituted prior to use.

A "moiety" or "group" refers to one of the portions into which something, such as a molecule, is divided (e.g., a functional group, substituent group, or the like). For example, a probe may be considered an oligonucleotide that optionally comprises a quencher moiety, a labeling moiety, or the like.

The term "nucleic acid" refers to a polymer of monomers that can be corresponded to a ribose nucleic acid (RNA) or deoxyribose nucleic acid (DNA) polymer, or analog thereof. This includes polymers of nucleotides such as RNA and DNA, as well as modified forms thereof, peptide nucleic acids (PNAs), locked nucleic acids (LNA™), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, an amplicon, an oligonucleotide, a primer, a probe, etc. A nucleic acid can be e.g., single-stranded or double-stranded. Unless otherwise indicated, a particular nucleic acid sequence optionally comprises or encodes complementary sequences, in addition to any sequence explicitly indicated.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (Jenkins et al. (1995) *Chem. Soc. Rev.* pp 169-176, which is incorporated by reference). Several nucleic acid analogs are also described in, e.g., Rawls, *C & E News* Jun. 2, 1997 page 35, which is incorporated by reference. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d] pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

A "nucleotide incorporating biocatalyst" refers to a catalyst that catalyzes the incorporation of nucleotides into a nucleic acid. Nucleotide incorporating biocatalysts are typically enzymes. An "enzyme" is a protein-based catalyst that acts to reduce the activation energy of a chemical reaction involving other compounds or "substrates." A "nucleotide incorporating enzyme" refers to an enzyme that catalyzes the incorporation of nucleotides into a nucleic acid. Exemplary nucleotide incorporating enzymes include, e.g., DNA polymerases, RNA polymerases, terminal transferases, reverse transcriptases, telomerases, polynucleotide phosphorylases, and the like. Other biocatalysts may be DNA-based ("DNAzymes") or RNA-based ("ribozymes"). A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR-CLONING NUCLEIC ACID SEQUENCES," issued Jul. 28, 1987 to Mullis et al., which are both incorporated by reference. As used herein, a thermostable polymerase is typically suitable for use in a temperature cycling reaction such as a PCR or a 5'-nuclease reaction. For a thermostable polymerase, enzymatic activity refers to the catalysis of the polymerization of the nucleotides in the proper manner to form primer extension products that are complementary to a template nucleic acid.

An "oligonucleotide" or a "polynucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known in the art. All of these references are incorporated by reference.

A "thiazine dye" refers to any of a class of organic chemical compounds containing a tricyclic aromatic fused ring system, where two of the carbons in the middle ring are replaced by a nitrogen atom and a sulfur atom. Exemplary thiazine dyes include methylene blue, methylene green, thionin, 1,9-dimethylmethylene blue, sym-dimethylthionin, toluidine blue O, new methylene blue, methylene violet bernthsen, azure A, azure B, and azure C.

The term "template nucleic acid" or "target nucleic acid" refers to a nucleic acid that is to be amplified, detected, or otherwise analyzed. "Target nucleic acid variants" are nucleic acid sequences that are known to occur, or are thought to possibly occur in a sample, and that are similar or nearly identical to the target nucleic acid sequence or to each other except for a relatively small number of nucleotide changes. The changes may occur as an insertion or deletion, or may be point mutations. As an example, variants of an infectious virus (e.g., HIV, HBV, HCV, etc.) nucleic acid are target nucleic acid variants. In some embodiments, The difference between two variants in a target nucleic acid sequence will occur at no more than 1, 2, 3, 4, 5, 6, 7, 8, 9, or 10 nucleotide positions. As described in more detail herein, in some embodiments, the target nucleic acid has a region of sequence at which a primer sequence can hybridize under amplification conditions, and adjacent (i.e., within the resulting amplicon, not necessarily directly adjacent) to that position, the sequence variation will occur such that when the primer is extended to form an amplicon, the amplicon comprises at least one variant position.

As used herein, the term "Tm" is used in reference to the "melting temperature." The melting temperature is the temperature at which one half of a population of double-stranded polynucleotides or nucleobase oligomers (e.g., hybridization complexes), in homoduplexes or heteroduplexes, become dissociated into single strands. The prediction of a Tm of a duplex polynucleotide takes into account the base sequence as well as other factors including structural and sequence characteristics and nature of the oligomeric linkages. Methods for predicting and experimentally determining Tm are known in the art.

For example, a Tm is traditionally determined by a melting curve, where a duplex nucleic acid molecule is heated in a controlled temperature program, and the state of association/dissociation of the two single strands in the duplex is monitored and plotted until reaching a temperature where the two strands are completely dissociated. The Tm is read from this melting curve. Alternatively, a Tm can be determined by an annealing curve, where a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The Tm is read from this annealing curve.

It is not intended that the invention be limited to any particular method for the determination of Tm. Methods for the experimental determination of Tm are widely known in the art and are described in a variety of sources, e.g., Liew et al., "Genotyping of Single-Nucleotide Polymorphism by High-Resolution Melting of Small Amplicons," Clinical Chemistry 50(7):1156-1164 (2004); Reed and Wittwer "Sensitivity and Specificity of Single-Nucleotide Polymorphism Scanning by High-Resolution Melting Analysis," Clinical Chemistry 50(10):1748-1754 (2004); Zhou et al., "Closed-Tube Genotyping with Unlabeled Oligonucleotide Probes and a Saturating DNA Dye," Clinical Chemistry 50(8):1328-1335 (2004); and Zhou et al., "High-resolution DNA melting curve analysis to establish HLA genotypic identity," Tissue Antigens 64:156-164 (2004). Melting/annealing curve analysis instrumentation is commercially available from a variety of manufacturers.

As used herein, the term "sample" is used in its broadest sense, and refers to any material subject to analysis. The term "sample" refers typically to any type of material of biological origin, for example, any type of material obtained from animals or plants. A sample can be, for example, any fluid or tissue such as blood or serum, and furthermore, can be human blood or human serum. A sample can be cultured cells or tissues, cultures of microorganisms (prokaryotic or eukaryotic), or any fraction or products produced from or derived from biological materials (living or once living). Optionally, a sample can be purified, partially purified, unpurified, enriched or amplified. Where a sample is purified or enriched, the sample can comprise principally one component, e.g., nucleic acid. More specifically, for example, a purified or amplified sample can comprise total cellular RNA, total cellular mRNA, cDNA, cRNA, or an amplified product derived there from.

The sample used in the methods of the invention can be from any source, and is not limited. Such sample can be an amount of tissue or fluid isolated from an individual or individuals, including, but not limited to, for example, skin, plasma, serum, whole blood, blood products, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc.

DETAILED DESCRIPTION OF THE INVENTION

I. Introduction

The present application provides for methods of efficiently detecting the presence or absence of a target nucleic acid wherein the target nucleic acid can have a number of different variants. The methods of the present invention allow for detection of target nucleic acid variants and allows for differentiation between variants, thus allowing for a determination of which target nucleic acid variant is present in a sample. One advantage of the invention is the ability to detect and differentiate between a relatively large number of potential target nucleic acid variants without the use of a "probe" such as is typically used in real-time amplification reactions. Thus, in some embodiments, the methods, reaction mixtures, and kits of the invention do not include a "probe" (i.e., a labeled oligonucleotide that is not extended by a polymerase but that hybridizes and is used to detect the presence or absence of a template or amplicon).

The present invention for useful for molecular diagnostics, pathogen, cancer, or other genotyping, detecting single nucleotide polymorphisms (SNPs), testing for drug resistant pathogens, or other applications where nucleic acid detection is desired.

In some embodiments, the present invention provides a method by which primer oligonucleotides, labeled with a light emitting label, are contacted to polynucleotides from a sample and are used to amplify a target nucleic, if present, from the sample. The primer sequences are designed such that the primer will hybridize to the target nucleic acid sequence during an amplification reaction, thereby allowing for amplification of the target nucleic acid. The resulting amplicon is designed to comprise sequences within the target sequence that can vary between eligible target nucleic acid variants. As an example, in some embodiments, it may be known that hepatitis C virus (HCV) nucleic acid sequences can occur in three variants. The primer is designed such that the resulting amplicon will comprise any of the three possible variants that may exist in the template. Thus, in some embodiments, when there are at least two template variants present, two or more amplicon variants can be generated from one labeled oligonucleotide. In such cases, in some embodiments, the Tm of the amplicons generated from the same labeled oligonucleotide will vary sufficiently (e.g., 5°C.) from each other such that the two or more amplicons can be distinguished a melting curve analysis.

The invention provides for differentiation of the presence of amplicons (including the light emitting label present on the primer) from different target nucleic acid variants by detecting the melting temperature of the resulting amplicons, wherein the potential amplicon from each target variant can be distinguished by having a different melting temperature. The melting temperature of the amplicons are readily determined due to the presence of a soluble light emission modifier that associates with double stranded nucleic acids but does not significantly associate with single stranded nucleic acids. The soluble light emission modifier, when associated with double stranded nucleic acids labeled with light emitting labels (e.g., the amplicons), alters the signal from the label such that the signal of the label when incorporated into single stranded nucleic acids can be distinguished from the signal of the same label when incorporated into double-stranded nucleic acids, thereby allowing for a melting temperature determination. For example, in some embodiments, the soluble light emission modifier quenches the signal from the label when the amplicon is double-stranded but does not significantly quench the signal when the amplicon is single-stranded.

One advantage of the methods of the present invention is that a relatively large number of different possible variants can be distinguished. The number of variants detected can be accommodated in the methods by at least two ways: (1) by using melting temperature to distinguish between different possible amplicons each having the same label, and (2) by using primers with different labels. These options can be used in combination to allow for a large number of different possible variants to be detected.

In a simple example of option (1), two variants can be detected by using a labeled primer that allows for production of an amplicon that could include either of the two possible variants. Which variant (assuming only one is present) occurs in a sample is determined by detecting the melting temperature (Tm) of the amplicon, wherein Tm1 is the melting temperature of the amplicon if variant 1 is present and Tm2 is the melting temperature of the amplicon if variant 2 is present, wherein Tm1 and Tm2 are different and distinguishable by the Tm determination method used. In some embodiments, the labeled primer is designed to detect 3, 4, 5, 6, 7, or more different variants, each differentiated from each other by Tm. The number of variants that can be detected by option (1) is limited by the number of different melting temperatures that can be distinguished using the variants to be detected. Note that more than one variant template can be in the sample and, if present, in some embodiments, both variants can be selected y detecting the presence or absence of each variant's amplicon by detecting each amplicon's signature Tm.

In a simple example of option (2) involving the same two variants discussed above, one primer labeled with a first light emitting label and a second primer labeled with a distinguishable second light emitting label are used to amplify polynucleotides in the sample. The two different primers are designed such that they hybridize to different target sequences such that a first primer only becomes integrated into an amplicon with variant 1 target nucleic acids, but does not become integrated into an amplicon with variant 2 target nucleic acids. Similarly, the second primer only becomes integrated into an amplicon with variant 2 target nucleic acids, but does not become integrated into an amplicon with variant 1 target nucleic acids. Variant 1 and variant 2 are then distinguished by the presence of signal from the label of primer 1 or from primer 2 in the double-stranded amplicon. The number of variants that can be detected by option (2) is limited by the number of different primer labels can be used and detected.

The methods of the invention are of particular use when options (1) and (2) are combined. For instance, where one desires to be able to detect more than 2 (e.g., 3, 4, 5, 6, 7, 8, 9, 10, 11, 12, etc., e.g., at least 3, at least 4, at least 5, at least 6, at least 8, etc.) variants, a certain number of variants can be "assigned" to a first labeled primer (i.e., a primer can be designed to amplify the certain number of variants, designated here for convenience as "primer 1 variants"), wherein each of the Tms of amplicons comprising the different "primer 1 variants" are different and thus can be distinguished. A second primer, labeled with a different label, is assigned to a second set of variants ("primer 2 variants"), again where each of the amplicons from these primer 2 variants have a different Tm. Following amplification and detection of signal of the primer labels in the presence of the soluble light emission modifier in a melting temperature determination assay, one can determine which variant was present based on which primer label is detected, and at what melt temperature the alteration of the label signal took place. This "option (1)/(2)" embodiment, is thus superior to prior art methods by allowing for efficient detection of a much larger number of variants than was previously practically possible. Note that the "½" option allows for a reduction in the number of primers and the number of different labels that would otherwise be necessary for detection of a set number of variants using standard multiplex reactions.

II. Primer Oligonucleotides

The primer oligonucleotides of the invention are designed such that the desired variant sequences are incorporated in an amplicon during an amplification reaction in the presence of the appropriate target nucleic acid variant sequence. Thus, for example, the primers can hybridize in an amplification reaction upstream of where the particular variation (e.g., a SNP or other distinguishing variation) occurs in the target nucleic acid. In some embodiments, the primer can be designed to hybridize to the relevant variation sequence. In some embodiments, the amplification reaction conditions are generally set such that absolute complementarity is not required to result in hybridization and primer extension. In other embodiments, the amplification reaction conditions are set such that the primer only hybridizes if there is absolute complementarity with the template.

Depending on the type of amplification reaction used, forward and reverse primers are provided for each amplicon to be generated. Thus, in some embodiments, a labeled forward primer and an unlabeled reverse primer is used to generate an amplicon. For example, the amplicon generated by the forward and reverse primer can be generated from any number of variant sequences such that the amplicon has a different Tm depending on which target variant is amplified. For the purposes of this discussion, "forward" and "reverse" can be interchanged.

Where more than one labeled primer is used (e.g., to detect a larger number of potential variants), each labeled primer can also have a corresponding reverse primer. Alternatively, the labeled primers can be designed to hybridize to different sequences on the target nucleic acid but nevertheless employ the same reverse primer in the amplification reaction. Those of skill in the art will appreciate that various combinations of forward and reverse primers can be used, depending on the number of differentially-labeled primers used, the target nucleic acid variants to be detected, etc.

Primers are generally of sufficient length and complementarity so that they selectively bind to target nucleic acids under selected conditions to permit polymerization-independent cleavage or polymerization-dependent cleavage to proceed. The exact length and composition of the primer will depend on many factors, including temperature of the annealing reaction, source and composition of the primer, etc. For example, depending on the complexity of the target sequence, the primer typically includes about 15-30 nucleotides, although it may contain more or fewer nucleotides.

In certain embodiments, modified nucleotides are included in primers. To illustrate, the introduction of modified nucleotide substitutions into oligonucleotide sequences can, e.g., increase the melting temperature of the oligonucleotides. In some embodiments, this can yield greater sensitivity relative to corresponding unmodified oligonucleotides even in the presence of one or more mismatches in sequence between the target nucleic acid and the particular oligonucleotide. Exemplary modified nucleotides that can be substituted or added in oligonucleotides include, e.g., C5-ethyl-dC, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-0-methyl Ribo-U, 2'-0-methyl Ribo-C, an 8-aza-dA, an 8-aza-dG, a 7-deaza-dA, a 7-deaza-dG, N4-ethyl-dC, N6-methyl-dA, etc. To further illustrate, other examples of modified oligonucleotides include those having one or more LNA™ monomers. Nucleotide analogs such as these are also described in, e.g., U.S. Pat. No. 6,639,059, issued Oct. 28, 2003 to Kochkine et al., U.S. Pat. No. 6,303,315, issued Oct. 16, 2001 to Skouv, and U.S. Pat. Application Pub. No. 2003/0092905, entitled by Kochkine et al. that published May 15, 2003, which are each incorporated by reference. Oligonucleotides comprising LNA™ monomers are commercially available through, e.g., Exiqon AIS (Vedbxk, DK).

III. Labels and Soluble Light Emission Modifiers

It will be appreciated that a wide range of different light emitting labels and soluble light emission modifiers can be used such that their combination allows for alteration (e.g. quenching) of the signal of the label when the label is incorporated into a double stranded nucleic acid in the presence of the soluble light emission modifier compared to when the label is incorporated into a single stranded nucleic acid in the presence of the soluble light emission modifier.

Labels

As described herein, at least one primer for each amplification reaction is labeled to permit detection of the resulting amplicon comprising the labeled primer sequence. In general, a label can be any moiety that can be attached to a nucleic acid and provide a detectable signal (e.g., a quantifiable signal). Signal for the label can be distinguished depending on whether the label is incorporated into double-stranded or single-stranded nucleic acids. Labels may be attached to oligonucleotides directly or indirectly by a variety of techniques known in the art. To illustrate, depending on the type of label used, the label can be attached to a terminal (5' or 3' end of an oligonucleotide primer) or a non-terminal nucleotide, and can be attached indirectly through linkers or spacer arms of various sizes and compositions. Using commercially available phosphoramidite reagents, one can produce oligonucleotides containing functional groups (e.g., thiols or primary amines) at either the 5' or 3' terminus via an appropriately protected phosphoramidite, and can label such oligonucleotides using protocols described in, e.g., Innis et al. (Eds.) *PCR Protocols: A Guide to Methods and Applications*, Elsevier Science & Technology Books (1990)(Innis), which is incorporated by reference.

Essentially any light emitting labeling moiety is optionally utilized to label a primer by techniques well known in the art. In some embodiments, for example, labels comprise a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128 (5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference.

To further illustrate, essentially any nucleic acid (and virtually any labeled nucleic acid, whether standard or non-standard) can be custom or standard ordered from any of a variety of commercial sources, such as The Midland Certified Reagent Company, The Great American Gene Company, ExpressGen Inc., Operon Technologies Inc., Proligo LLC, and many others.

Soluble Light Emission Modifiers

The light emission modifiers used in the reaction mixtures and other aspects of the invention typically include a variety of properties that make them well suited to modulate emissions of light from labeled oligonucleotides in various types of nucleic acid amplification reactions and assays. In some embodiments, these light emission modifiers non-covalently bind to both single-stranded nucleic acids (e.g., single-stranded probes) and to double-stranded nucleic acids (e.g., single-stranded probes hybridized to target nucleic acids). However, the light emission modifiers bind to signal stranded nucleic acids much more weakly than to double stranded nucleic acids. For example, some soluble light emission modifiers intercalate into double-stranded nucleic acids. As a result, the light emission modifiers significantly alter the signal of labeled double stranded nucleic acids compared to signal stranded nucleic acids, thereby allowing for a determination of whether the nucleic acids are single or double stranded. In some embodiments, a given light emission modifier is able to effectively modify the emission of light from a variety of different light-emitting moieties. In other words, the modifications (e.g., quenching) effected by these light emission modifiers are generally spectral overlap independent or universal and without being bound to any particular theory of operation, likely occur by way of ground state complex formation. This allows for the use of multiple labels with one light emission modifier. Of course, more than one light emission modifier can be used as desired.

Many different light emission modifiers are suitable for use in the reaction mixtures and other aspects of the invention. Light emission modifiers are soluble nucleic acid binding compounds that are capable of modifying the emission of light from labeled oligonucleotides, e.g., labeled with a fluorescent label, optionally at reaction temperatures commonly used in performing real-time PCR reaction steps, such as at annealing temperatures of at least about 40° C. In some embodiments, for example, the light emission modifiers of the invention include various diazine and thiazine dyes. Exemplary diazine dyes that can be used as light emission modifiers include, e.g., azocarmine dyes (e.g., azocarmine A, azocarmine B ($C_{28}H_{17}N_3O_9S_3Na_2$), azocarmine G ($C_{28}H_{18}N_3O_6S_2Na$), etc.), phenazine dyes, oxazine dyes (e.g., Celestine blue ($C_{17}H_{18}ClN_3O_4$), etc.), diethylsafraninazodimethylaniline chloride (i.e., Janus Green B or Diazine Green 5 ($C_{30}H_{31}N_6Cl$)), and the like. The chemical structures of some of these diazine dyes are presented in Table I.

TABLE I

AZOCARMINE G

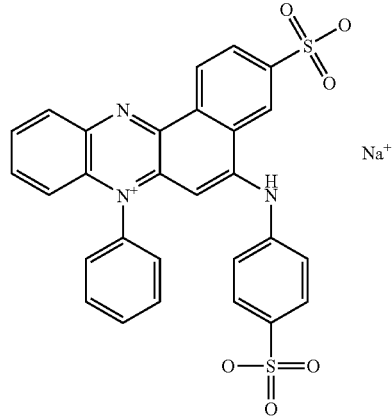 [SMILES: O=S(=O)(O)c1ccc(Nc2cc3c(nc4ccccc4[n+]3-c3ccccc3)c3ccc(S(=O)(=O)O)cc23)cc1 ; [Na+]]

CELESTINE BLUE

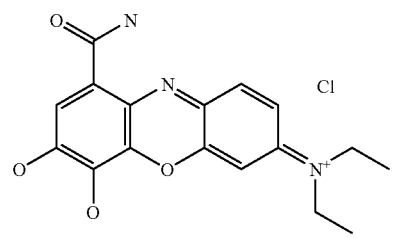 [SMILES: CC[N+](CC)=c1ccc2nc3c(C(N)=O)cc(O)c(O)c3oc-2c1 ; Cl]

TABLE I-continued

JANUS GREEN B

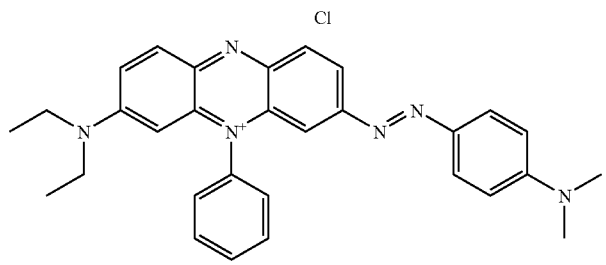 [SMILES: Cl ; CCN(CC)c1ccc2nc3ccc(/N=N/c4ccc(N(C)C)cc4)cc3[n+](-c3ccccc3)c2c1]

To further illustrate, exemplary thiazine dyes that can be used as light emission modifiers include, e.g., methylene blue ($C_{16}H_{18}ClN_3S$), methylene green ($C_{16}H_{17}ClN_4O_2S$), thionin ($C_{12}H_{10}ClN_3S$), sym-dimethylthionin, toluidine blue O ($C_{15}H_{16}N_3SCl$), new methylene blue ($C_{18}H_{22}ClN_3S$), methylene violet bernthsen, azure A ($C_{14}H_{14}ClN_3S$), azure B ($C_{15}H_{16}ClN_3S$), azure C ($C_{13}H_{12}ClN_3S$), and the like. The chemical structures of some of these thiazine dyes are presented in Table II.

TABLE II

| | |
|---|---|
| THIONIN | 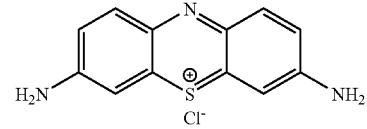 [SMILES: Nc1ccc2nc3ccc(N)cc3[s+]c2c1 ; [Cl-]] |
| AZURE C | 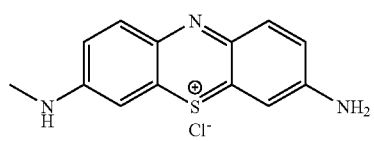 [SMILES: CNc1ccc2nc3ccc(N)cc3[s+]c2c1 ; [Cl-]] |
| AZURE A | 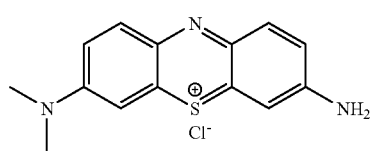 [SMILES: CN(C)c1ccc2nc3ccc(N)cc3[s+]c2c1 ; [Cl-]] |
| AZURE B | 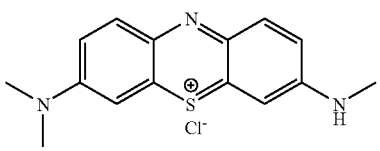 |
| SYM-DIMETHYLTHIONIN | 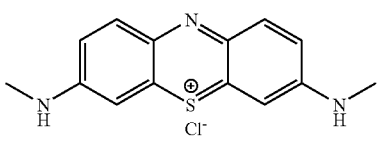 |
| METHYLENE VIOLET BERNTHSEN | 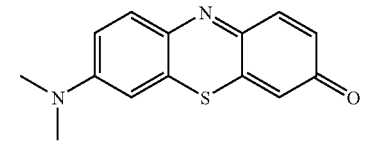 [SMILES: CN(C)c1ccc2nc3ccc(=O)cc-3sc2c1] |
| METHYLENE BLUE | 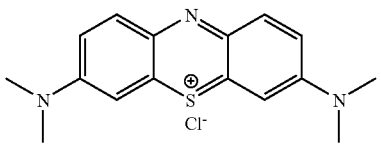 |

TABLE II-continued

| | |
|---|---|
| 1,9-DIMETHYLMETHYLENE BLUE | |
| NEW METHYLENE BLUE | |
| TOLUIDINE BLUE O | |
| METHYLENE GREEN | |

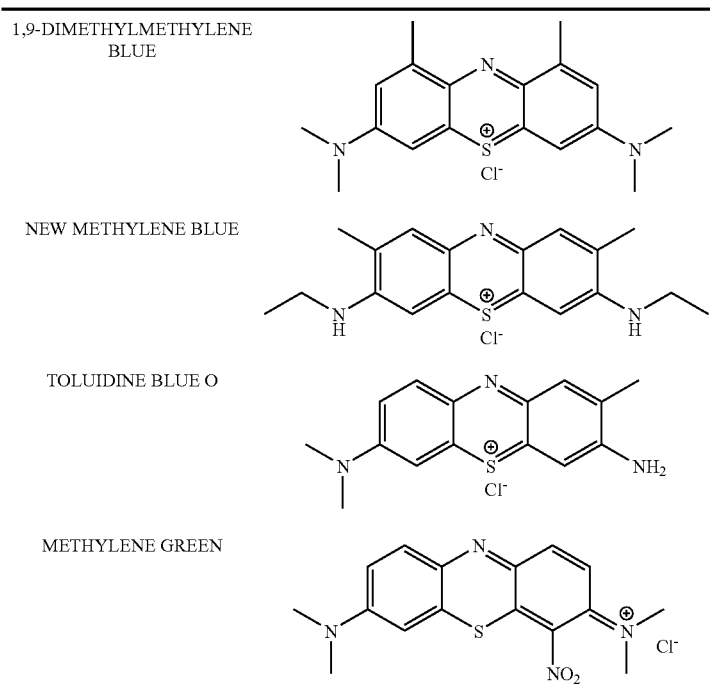

The amount of the particular light emission modifier included in a given reaction mixture typically depends on the extent of modification sought. Typically, the extent of light emission modification is proportional to the amount of light emission modifier present in a reaction mixture. Although other quantities are optionally utilized, in some embodiments, light emission modifiers are present at between about 5 µg/mL of the reaction mixture and about 100 µg/mL of the reaction mixture, e.g., at between about 10 µg/mL of the reaction mixture and about 75 µg/mL of the reaction mixture, e.g., at between about 15 µg/mL of the reaction mixture and about 50 µg/mL of the reaction mixture (e.g., about 20 µg/mL, about 30 µg/mL, about 40 µg/mL, etc.). In some embodiments, reaction mixtures include light emission modifier concentrations that are in excess of amplicon concentrations. In some embodiments, more than one light emission modifier can be used in the same reaction mixture. In these embodiments, the different light emission modifiers are optionally present at the same or at different concentrations in the particular reaction mixture. As one example, a reaction mixture may include 20 µg of new methylene blue per mL of the reaction mixture and 30 µg of methylene blue per mL of the reaction mixture. Light emission modifiers are readily available from various commercial suppliers including, e.g., Sigma-Aldrich Corp. (St. Louis, Mo., USA).

IV. Target Nucleic Acids

Target nucleic acids can come from a biological or synthetic source. The target can be, for example, DNA or RNA. Generally, where amplicons are generated, the amplicons will be composed of DNA, though ribonucleotides or synthetic nucleotides can also be incorporated into the amplicon. Where one wishes to detect an RNA, the amplification process will typically involve the use of reverse transcription, including for example, reverse transcription PCR(RT-PCR).

Specific target sequences can include, e.g., viral nucleic acids (e.g., HIV, HBV, HCV, HPV), bacterial nucleic acids (e.g., *S. aureus, Neisseria meningitidis, Plasmodium falciparum, Chlamydia muridarum, Chlamydia trachomatis*), fungal nucleic acids, or nucleic acids from animals or plants. In some embodiments, the target nucleic acids are human nucleic acids. In some embodiments, the target nucleic acids are, for example, human genetic regions that may include variants associated with disease (e.g., cancer (including but not limited to oncogenes and tumor suppressor genes), diabetes, etc.).

V. Amplification

In practicing the methods of the present invention, many conventional techniques in molecular biology are optionally utilized. These techniques are well known and are explained in, for example, Ausubel et al. (Eds.) *Current Protocols in Molecular Biology*, Volumes I, II, and III, (1997) (Ausubel 1), Ausubel et al. (Eds.), *Short Protocols in Molecular Biology: A Compendium of Methods from Current Protocols in Molecular Biology*, 5$^{th}$ Ed., John Wiley & Sons, Inc. (2002) (Ausubel 2), Sambrook et al., *Molecular Cloning: A Laboratory Manual*, 3rd Ed., Cold Spring Harbor Laboratory Press (2000) (Sambrook), Berger and Kimmel, *Guide to Molecular Cloning Techniques: Methods in Enzymology*, Volume 152, Academic Press, Inc. (Berger), Vorbruggen et al., *Handbook of Nucleoside Synthesis*, Organic Reactions Series, #60, John Wiley & Sons, Inc. (2001), Gait (Ed.) *Oligonucleotide Synthesis*, Oxford University Press (1984), Hames and Higgins, *Nucleic Acid Hybridization*, Practical Approach Series, Oxford University Press (1997), and Hames and Higgins (Eds.) *Transcription and Translation*, Practical Approach Series, Oxford University Press (1984), all of which are incorporated by reference.

Examples of general types of nucleic acid analysis technologies that can be used or adapted for use to analyze target nucleic acids in or from the reactions mixtures of the invention include various nucleic acid amplification assays. Nucleic acid amplification tests can have greater sensitivity than other approaches to nucleic acid analysis. This sensitivity, which is further improved with the use of the light emission modifiers of the invention, is typically attributable to their ability to produce a positive signal from as little as a single copy of the target nucleic acid. Amplification methods that are optionally utilized or adapted to detect target nucleic acids include, e.g., various polymerase, ligase, or reverse-transcriptase mediated amplification methods, such as the polymerase chain reaction (PCR), the ligase chain reaction (LCR), reverse-transcription PCR (RT-PCR), NASBA, TMA, SDA and the like. Additional details regarding the use of these and other amplification methods and various approaches to sample preparation for these assays can be found in any of a variety of standard texts, including, e.g., Berger, Sambrook, Ausubel 1 and 2, and Innis, which are referred to above. Various commercial nucleic acid amplification assays that are optionally adapted for use with the light emission modifiers and methods of the invention generally differ in their amplification methods and their target nucleic acid sequences. Examples of these commercial tests include the AMPLICOR® and COBAS AMPLICOR® assays (Roche Diagnostics Corporation, Indianapolis, Ind., USA), which use polymerase chain reactions (PCR); the LCx® test (Abbott Laboratories, Abbott Park, Ill., USA), which uses ligase chain reactions (LCR); the BDProbeTec™ ET test (Becton, Dickinson and Company, Franklin Lakes, N.J., USA), which uses strand displacement amplification (SDA); the NucliSens EasyQ assay (bioMerieux, Durham, N.C.), which uses nucleic acid sequence-based amplification (NASBA); and the APTIMA™ assay (Gen-Probe, Inc., San Diego, Calif., USA), which uses transcription-mediated amplification (TMA). Nucleic acid amplification and detection is described further below.

Template-dependent extension of primers is generally catalyzed by a nucleotide incorporating biocatalyst (e.g., a polymerase, etc.) in the presence of adequate amounts of the four deoxyribonucleoside triphosphates (dATP, dGTP, dCTP, and dTTP) or analogs in a reaction mixture that also includes light emission modifiers and appropriate salts, metal cations, and buffers. Reaction mixtures are described further above. Suitable nucleotide incorporating biocatalysts are enzymes known to catalyze primer and template-dependent DNA synthesis and possess the 5' to 3' nuclease activity. Exemplary DNA polymerases of this type include *E. coli* DNA polymerase I, Tth DNA polymerase, *Bacillus stearothermophilus* DNA polymerase, Taq DNA polymerase, *Thermus* sp. ZO5 DNA polymerase, *Thermatoga maritima* DNA polymerase, *Thermatoga neopolitana* DNA polymerase, and *Thermosipho africanus* DNA polymerase. The reaction conditions for catalyzing DNA synthesis with these DNA polymerases are well known in the art. Typically, the nucleotide incorporating biocatalyst efficiently cleaves the probe and releases labeled fragments so that a detectable signal is directly or indirectly generated.

The products of the synthesis are generally duplex molecules that include the template strands and the primer extension strands. Byproducts of this synthesis are probe fragments, which can include a mixture of mono-, di- and larger nucleotide fragments. Repeated cycles of denaturation, probe and primer annealing, and primer extension and probe cleavage result in the exponential accumulation of the region defined by the primers and the exponential generation of labeled fragments. Sufficient cycles are run to achieve a detectable amount of probe fragments, which is generally several orders of magnitude greater than background signal.

The use of light emission modifiers as described herein can effectively reduce the number of cycles run before a detectable signal is produced relative to assays that do not reduce these background signals.

In certain embodiments, PCR reactions are carried out as an automated process, which utilizes a thermostable enzyme. In this process the reaction mixture is cycled through a denaturing step, a primer (and optionally, probe) annealing step, and a synthesis step in which cleavage and displacement occur simultaneously with primer dependent template extension. In some embodiments, the methods described herein are performed using a system. Such systems are described in greater detail below. Optionally, thermal cyclers, such as those commercially available from, e.g., Applied Biosystems (Foster City, Calif., USA), which are designed for use with thermostable enzymes, may be utilized.

Thermostable polymerases are typically used in automated processes that effect the denaturation of double stranded extension products by exposing them to a elevated temperatures (e.g., about 95° C.) during the PCR cycle. For example, U.S. Pat. No. 4,889,818, entitled "PURIFIED THERMOSTABLE ENZYME," issued to Dec. 26, 1989 to Gelfand et al., which is incorporated by reference, discloses a representative thermostable enzyme isolated from *Thermus aquaticus*. Additional representative thermostable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermatoga neopolitana, Thermosipho africanus, Thermococcus littoralis,* and *Methanothermus fervidus*.

Hybridization of probes to target nucleic acids can be accomplished by choosing appropriate hybridization conditions. The stability of the probe:target nucleic acid hybrid is typically selected to be compatible with the assay and washing conditions so that stable, detectable hybrids form only between the probes and target nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins.

Other examples of such reagents and chemicals include divalent ions, polyvalent ions and intercalating substances such as ethidium bromide, actinomycin D, psoralen, and angelicin.

VI. Melting Temperature

The invention provides methods for determining the melting temperature (Tm) of a hybridization complex, where these methods use the soluble light emission modifier technology taught herein. The Tm determinations use a soluble light emission modifier (i.e., a soluble quencher) system to monitor the duplex melting curve or annealing curve.

A primer labeled with a suitable light emitting moiety (e.g., a donor) is incorporated into a double-stranded amplicon. Any nucleic acid duplex is characterized by a particular Tm at a give set of hybridization conditions. It is this feature that makes Tm determinations useful in applications such as diagnostics (e.g., SNP detection, mutation detection and mutation scanning, viral genotyping, testing for drug resistant strains etc.) and allows for differentiation between variants.

Either before, during or after formation of the duplex, the reaction is admixed with a suitable soluble light emission modifier (e.g., a quencher). This soluble quencher comprises a thiazine dye or a diazine dye, where the soluble quencher is capable of quenching the light emitting moiety incorporated into the amplicon (thus forming a donor-acceptor pair). It is noted that thiazine, phenothiazine, cationic thiazines, thiazinium, and phenothiazinium are all synonyms for a generic name for the family of dyes with fused 3-ring aromatic system containing a nitrogen and a sulfur in the middle ring. Furthermore, in addition to the particular thiazine and diazine structures taught herein, related structural variants of these molecules that retain the soluble quencher property can also be used with the methods of the invention, and are encompassed within the scope of the invention.

A thiazine dye or diazine dye soluble quencher acts by binding to both single and double-stranded nucleic acid, but has reduced affinity for single-stranded nucleic acid. It is contemplated that the binding to the single stranded nucleic acids could be due to partial secondary structures in the random coil state. Without being bound to any particular theory, it is believed that the predominant binding mode is through intercalation, but minor and major groove binding is also possible depending on the sequence context and hybridization conditions (see, Rohs et al. (2000) *J. Am. Chem. Soc.*, 122:2860-2866; and Tuite et al. (1994) *J. Am. Chem. Soc.*, 116:7548-7556). Thus, the fluorescence donor label attached to the primer that forms the hybridization complex with a target polynucleotide is subject to a quenching effect by the intercalating soluble quencher that has an affinity for double-stranded nucleic acid due to the close proximity of the quencher to the donor moiety in the amplicon (from the incorporated primer). However, an understanding of the molecular mechanisms of the quenching phenomenon is not required to make or use the invention.

If the solution containing the hybridization complex is heated (as in the melting curve Tm analysis), the amplicon eventually dissociates (i.e., is no longer double-stranded) from the target polynucleotide, thereby reducing the affinity of the quencher for the nucleic acid, resulting in reduced proximity of the soluble quencher to the donor and an increase in fluorescence from the donor is observed. Thus, the formation/dissociation of hybridization complexes in a reaction can be monitored by the use of a system having a soluble quencher.

Following formation of the duplex under conditions where base-pairing can occur, the temperature of the target hybridization complex reaction is raised and the emission from the donor is measured and monitored over a range of temperatures, thus forming a melting curve. A temperature range of, for example, about 20° C. to about 95° C. can be used. Alternatively, the amplicon and soluble quencher can start at an elevated temperature (e.g., about 95° C.), and the donor emission is monitored while the temperature of the reaction is lowered (e.g., to about 20° C.), thus generating an annealing curve.

In either case of an annealing curve or a melting curve, the measured emission from the donor is correlated with a particular duplex association/dissociation value, and a Tm is derived where the Tm is that temperature at which one half of a population of hybridization complexes becomes dissociated into single strands.

Examples of Tm determinations using soluble light emission modifiers and double stranded labeled nucleic acids can be found in, e.g., Examples 19-22 of U.S. Patent Publication No. 2007/0020664, published Jan. 25, 2007.

VII. Reaction Mixtures

The reaction mixtures of the invention typically include selected amounts of light emission modifiers and labeled oligonucleotides, as described herein. In addition, reaction mixtures also generally include various reagents that are useful in performing nucleic acid amplification or detection reactions, such as real-time PCR monitoring. Exemplary nucleic acid amplification reagents include, e.g., primer nucleic acids, template or target nucleic acids, nucleotide incorporating biocatalysts (e.g., DNA polymerases, etc.), extendible nucleotides, terminator nucleotides, buffers, salts, amplicons, glycerol, metal ions, dimethyl sulfoxide (DMSO), poly rA (a carrier nucleic acid for low copy targets), and the like. The nucleotide incorporating biocatalysts (e.g., DNA polymerases) in the reaction mixtures can have or lack various activities (e.g., 5'→3" nuclease activity) so long as the biocatalyst is capable of extending a primer in an amplification reaction under suitable amplification conditions. In some embodiments, for example, nucleic acid amplification reactions are performed utilizing these reaction mixtures to effect the detection of target nucleic acids in samples, e.g., to aid in the diagnosis and/or prognosis of diseases.

Reaction mixtures are generally produced by combining selected light emission modifiers and labeled oligonucleotides with quantities of the nucleic acid amplification reagents that are sufficient for performing the particular nucleic acid amplification method selected. The quantities of nucleic acid amplification reagents to be included in a given reaction mixture are well-known to persons of skill in the art in view of the selected nucleic acid amplification method. To illustrate, however, primer nucleic acids and extendible nucleotides (e.g., four dNTPs (dGTP, dCTP, dATP, dTTP)) are each present in a large molar excess in the reaction mixtures in certain embodiments. Probe and primer nucleic acids that can be utilized in the reaction mixtures of the invention are described herein. Suitable extendible nucleotides are readily available from many different commercial suppliers including, e.g., Roche Diagnostics Corporation (Indianapolis, Ind., USA), Amersham Biosciences Corp. (Piscataway, N.J., USA), Applied Biosystems (Foster City, Calif., USA), and the like.

The nucleotide incorporating biocatalysts utilized in the reaction mixtures and other aspect of the invention typically comprise enzymes, such as polymerases, terminal transferases, reverse transcriptases, telomerases, polynucleotide phosphorylases, and the like. In certain embodiments, for example, the enzyme includes a 5'-3' nuclease activity, a 3'-5' exonuclease activity, and/or is a thermostable enzyme. The enzyme is optionally derived from an organism, such as *Thermus antranikianii, Thermus aquaticus, Thermus caldophilus, Thermus chliarophilus, Thermus filiformis, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Anaerocellum thermophilum, Bacillus caldotenax, Bacillus stearothermophilus*, or the like.

In certain embodiments, additional reagents are also added to the reaction mixtures of the invention. To illustrate, reaction mixtures also optionally include pyrophosphatases (e.g., a thermostable pyrophosphatase), e.g., for use in minimizing pyrophosphorolysis, dUTP and uracil N-glycosylase (UNG) (e.g., a thermostable UNG), e.g., to protect against carry-over contamination, and the like.

In some embodiments, the reaction mixture comprises at least one target nucleic acid and:

(1) at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;

at least one soluble light emission modifier, which, when the modifier binds double stranded DNA incorporating the labeled oligonucleotide, alters (e.g., quenches) light emission from the first label compared to light emission of the first label in the presence of the soluble light emission modifier when the labeled oligonucleotide is single-stranded; and a single or double-stranded first amplicon polynucleotide, wherein the first amplicon polynucleotide comprises (e.g., at the 5' end of a strand of the amplicon) the label and the sequence of the labeled oligonucleotide; and optionally (2) a second labeled oligonucleotide comprising a second label, which second label comprises at least one light emitting moiety and wherein at least a subsequence of the second labeled oligonucleotide is sufficiently complementary to at least a second subsequence of the target nucleic acid that may occur in at least two variants such that the second labeled oligonucleotide hybridizes with the second target nucleic acid under the selected condition, and wherein signal from the second label can be distinguished from the signal of the first label (and if present the third and fourth label), wherein the at least one soluble light emission modifier, when intercalated in double stranded DNA incorporating the second labeled oligonucleotide alters (e.g., quenches) light emission from the second label compared to light emission of the second label when the second labeled oligonucleotide is single-stranded in the presence of the soluble light emission modifier; and a single or double-stranded second amplicon polynucleotide, wherein the second amplicon polynucleotide comprises (e.g., at the 5' end of a strand of the amplicon) the label and the sequence of the second labeled oligonucleotide and optionally (3) a third labeled oligonucleotide comprising a third label, which third label comprises at least one light emitting moiety and wherein at least a subsequence of the third labeled oligonucleotide is sufficiently complementary to at least a third subsequence of the target nucleic acid that may occur in at least two variants such that the third labeled oligonucleotide hybridizes with the third target nucleic acid under the selected condition, and wherein signal from the third label can be distinguished from the signal of the first and second label, wherein the at least one soluble light emission modifier, when intercalated in double stranded DNA incorporating the third labeled oligonucleotide alters (e.g., quenches) light emission from the third label compared to light emission of the third label when the third labeled oligonucleotide is single-stranded in the presence of the soluble light emission modifier; and a single or double-stranded third amplicon polynucleotide, wherein the third amplicon polynucleotide comprises (e.g., at the 5' end of a strand of the amplicon) the label and the sequence of the third labeled oligonucleotide; and optionally (4) a fourth labeled oligonucleotide comprising a fourth label, which fourth label comprises at least one light emitting moiety and wherein at least a subsequence of the fourth labeled oligonucleotide is sufficiently complementary to at least a fourth subsequence of the target nucleic acid that may occur in at least two variants such that the fourth labeled oligonucleotide hybridizes with the fourth target nucleic acid under the selected condition, and wherein signal from the fourth label can be distinguished from the signal of the first and second and third label, wherein the at least one soluble light emission modifier, when intercalated in double stranded DNA incorporating the fourth labeled oligonucleotide alters (e.g., quenches) light emission from the fourth label compared to light emission of the fourth label when the fourth labeled oligonucleotide is single-stranded in the presence of the soluble light emission modifier; and a single or double-stranded fourth amplicon polynucleotide, wherein the fourth amplicon polynucleotide comprises (e.g., at the 5' end of a strand of the amplicon) the label and the sequence of the fourth labeled oligonucleotide.

In some embodiments, there is at least two or more different amplicons comprising the sequence and label of any of one (or two, three or four) of the above-described labeled oligonucleotides. These would be generated, for example, where two variant templates were in the reaction mixture and so two amplicons were generated. In some embodiments, where there is more than one amplicon generated from the same labeled oligonucleotide, the different amplicon variants have a melting temperature at least 5° C. different from each other, thereby allowing for detection of each in a melting curve analysis.

In some embodiments, amplicons derived from different labeled oligonucleotides comprise at least 5, 10, 15, 20 or more contiguous nucleotides in common. In some embodiments, amplicons derived from different labeled oligonucleotides are generated from a common gene or viral or bacterial source (for example, each amplicon is an amplified HPV nucleic acid). In some of these embodiments, amplicons derived from different labeled oligonucleotides do not comprise at least 5, 10, 15, 20 or more contiguous nucleotides in common.

VIII. Kits

The reaction mixtures or components thereof (e.g., primers and/or light emission modifiers) employed in the methods of the present invention are optionally packaged into kits. In addition, the kits may also include suitably packaged reagents and materials needed for target nucleic acid hybridization, amplification, and detection, such buffers, enzymes, DNA standards, salts, metal ions, primers, extendible or terminator nucleotides, glycerol, dimethyl sulfoxide, poly rA, etc. as well as instructions for conducting a particular assay. Kit components, such as probes and light emission modifiers are typically provided in one or more containers. In some of these embodiments, the kits further include at least one pyrophosphatase (e.g., a thermostable pyrophosphatase), e.g., for use in minimizing pyrophosphorolysis, and/or uracil N-glycosylase (UNG), e.g., for use in applications where protection against carry-over contamination is desirable. Two or more of the kit components may be packaged within the same container.

IX. Systems

In some embodiments, the invention provides integrated systems for making Tm determinations. The systems can include instrumentation and means for interpreting and analyzing collected data, especially where the means for deriving the Tm comprise algorithms and/or electronically stored information (e.g., collected fluorescence data, predetermined Tm correlations, etc). Each part of an integrated system can be functionally interconnected, and in some cases, physically connected. In some embodiments, the integrated system is automated, where there is no requirement for any manipulation of the sample or instrumentation by an operator following initiation of the Tm analysis.

A system of the invention can include instrumentation. For example, the invention can include a detector such as a fluorescence detector (e.g., a fluorescence spectrophotometer). A detector or detectors can be used in conjunction with the invention, e.g., to monitor/measure the emission from the light emitting moiety on the Tm probe. A detector can be in the form of a multiwell plate reader to facilitate the high-throughput capacity of the Tm assay.

In some embodiments, the integrated system includes a thermal cycling device, or thermocycler, for the purpose of controlling the temperature of the Tm melting analysis. In some embodiments, the thermal cycling device and the detector are an integrated instrument, where the thermal cycling and emission detection (e.g., fluorescence detection) are done in the same device.

A detector, e.g., a fluorescence spectrophotometer, can be connected to a computer for controlling the spectrophotometer operational parameters (e.g., wavelength of the excitation and/or wavelength of the detected emission) and/or for storage of data collected from the detector (e.g., fluorescence measurements during a melting curve analysis). The computer may also be operably connected to the thermal cycling device to control the temperature, timing, and/or rate of temperature change in the system. The integrated computer can also contain the "correlation module" where the data collected from the detector is analyzed and where the Tm of the target hybridization complex is determined (electronically). In some embodiments, the correlation module comprises a computer program that calculates the Tm based on the fluorescence readings from the detector, and in some cases, optionally derives viral genotype information of a sample based on the Tm result. In some embodiments, the correlation module compares the Tm of the sample with a database (or table) of Tm values for known variant types (e.g., known viral variants, known SNPs, etc.) to make a correlation between the Tm of the unknown sample and the variant genotype of the unknown sample.

In some aspects, a system of the invention for the determination of a Tm of a hybridization complex comprises a reaction mixture as described herein. The system also includes a thermal control device for regulating the temperature of the melting reaction over a range of temperatures, where the range of temperatures includes a temperature where essentially all probe molecules anneal with the hybridization target at a given set of hybridization conditions, a temperature where 50% of the target hybridization complexes are dissociated, and a temperature where essentially no probe molecules anneal with the hybridization target and essentially no hybridization complexes are present at the hybridization conditions. The system can further include a detector for measuring the signal from the melting reaction over the range of temperatures; and also a correlation module that is operably coupled to the detector and receives signal measurements over the range of temperatures, where the correlation module correlates the signal intensity with the presence of a hybridization complex comprising the probe and the hybridization target in admixture with the soluble light emission modifier as a function of temperature, thereby determining the Tm of the target hybridization complex. In some aspects, the light emitting moiety on the probe is a FRET donor moiety.

The invention also provides systems for detecting target nucleic acids. The system includes one or more labeled oligonucleotides and one or more light emission modifiers as described herein. In certain embodiments, the oligonucleotides are arrayed on a solid support, whereas in others, they are provided in one or more containers, e.g., for assays performed in solution. The system also includes at least one detector (e.g., a spectrometer, etc.) that detects nucleic acids and/or amplicons thereof from the sample. In addition, the systems also optionally include at least one thermal modulator (e.g., a thermal cycling device, etc.) operably connected to the container or solid support to modulate temperature in the container or on the solid support, and/or at least one fluid transfer component (e.g., an automated pipettor, etc.) that transfers fluid to and/or from the container or solid support, e.g., for performing one or more nucleic acid amplification techniques and/or nucleic acid hybridization assays in the container or on the solid support.

Detectors are typically structured to detect detectable signals produced, e.g., in or proximal to another component of the given assay system (e.g., in container, on a solid support, etc.). Suitable signal detectors that are optionally utilized, or adapted for use, herein detect, e.g., fluorescence, phosphorescence, radioactivity, absorbance, refractive index, luminescence, mass, or the like. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, scanning detectors, or the like. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, photometers, and the like. Detectors are also described in, e.g., Skoog et al., *Principles of Instrumental Analysis*, 5$^{th}$ Ed., Harcourt Brace College Publishers (1998) and Currell, *Ana-* lytical Instrumentation: Performance Characteristics and Quality, John Wiley & Sons, Inc. (2000), both of which are incorporated by reference.

The systems of the invention also typically include controllers that are operably connected to one or more components (e.g., detectors, thermal modulators, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

EXAMPLE

Materials and Methods for Amplicon Melt with New Methylene Blue

Primers

This assay utilized genotype specific labeled primers only, no probes. The primers are generally labeled with FAM, HEX, JA270 or Cy5.5 on the 5' end of either the upsteam, downstream or both primers. Primers with an internal label may also be used. Primers are generally 16 base pairs or longer, and are designed to generate amplicons of varying length and melt temperature.

Master Mix

New Methylene Blue was added to the PCR master mix as a liquid quencher at 0.00625 µg/µl. ZO5 Gold polymerase was used at 60 U final concentration. Upstream and downstream primers were used in equal amounts of 0.25 uM each.

PCR and Melt Profile

The experiment was run on a Z480 with the following profile. Step 1, 50° C. for 2 min. step 2, 95° C. for 9 min. step 3, 95° C. 30 sec. followed by 55° C. for 45 sec.×60 cycles, step 4, 95° C. for 10 sec. followed by 40° C. for 2 min and 90° C. continuous 3 acquisitions per ° C.

Explanation of Graphs

HEX4S & HEX16

HPV types 45 and 16 were run under the above mentioned conditions. See, FIG. 1. A1: HEX45 represents HPV45 primers labeled with HEX at the 5' end of one primer and amplified in a background of HPV45 plasmid. C1: 16HEX is HPV16 primers internally labeled with HEX dye on one primer and amplified in a background of HPV16 plasmid. E11: HEX16/45+FAM31/39 is HPV16, 45, 31 and 39 primers combined and amplified in a background of HPV16, 45, 31 and 39 plasmids. B2 and D2 are no template controls.

Results

HPV16 and 45 melt peaks are visible at the correct Tms when multiplexed with the FAM labeled primers.

FAM31 and FAM39

Figure 2:
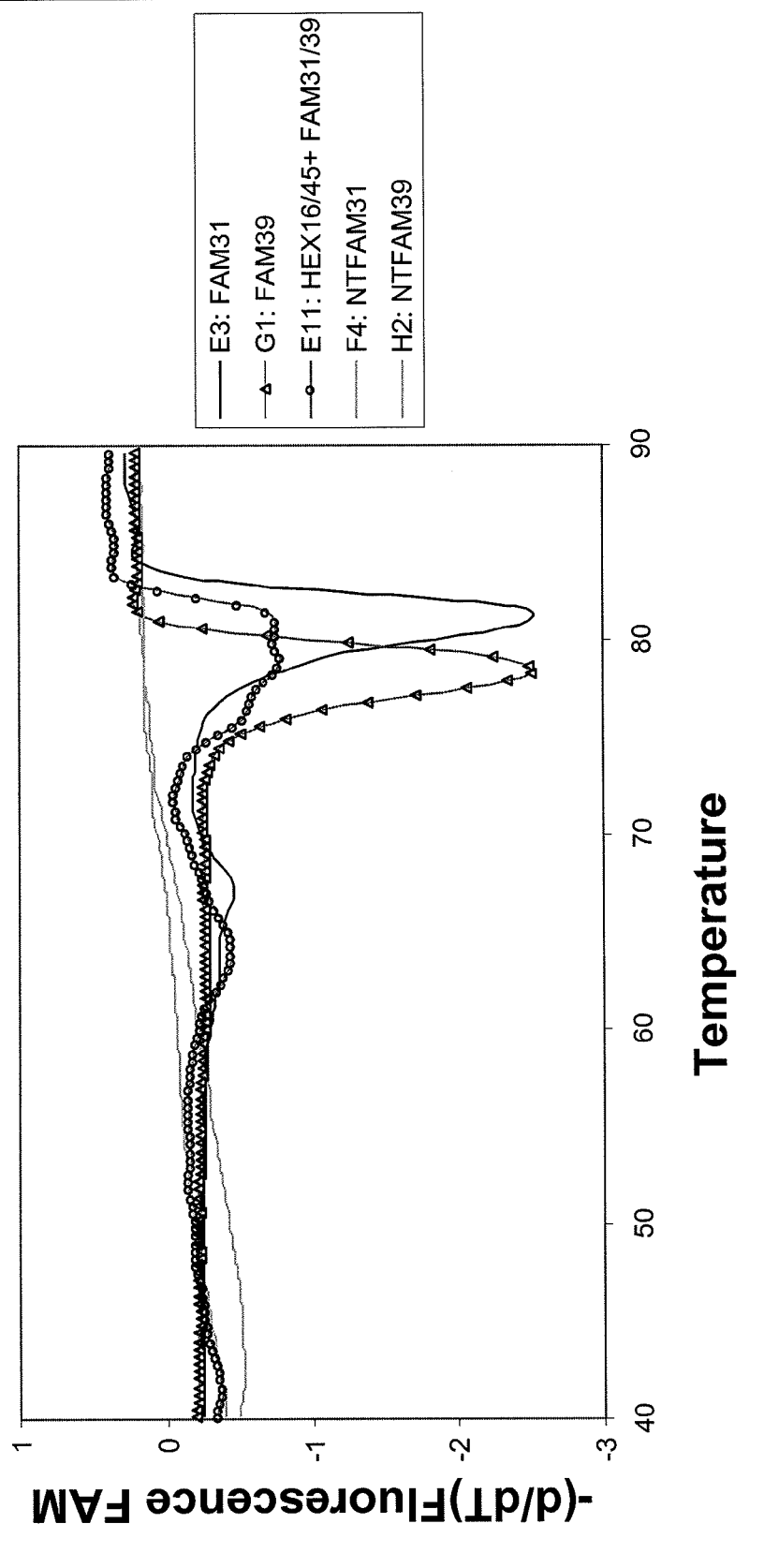
FIG. 2 illustrates melt curves of amplicons generated using HPV31 primers on an HPV31 template, HPV39 primers on a HPV39 template, or mixtures of both sets of primers and templates.

HPV types 31 and 39 were run under the above conditions. See, FIG. 2. E3: FAM31 represents HPV31 primers labeled with FAM at the 5' end of one primer and amplified with HPV31 plasmid. G1: FAM39 is HPV39 primers labeled with FAM at the 5' end of one primer and amplified with HPV39 plasmid. E11: HEX HEX16/45+FAM31/39 is HPV16, 45, 31 and 39 primers combined and amplified in a background of HPV16, 45, 31 and 39 plasmids. F2 and H2 are no template controls.

Results

HPV 31 and 39 have distinct melt peaks when amplified separately. However the melt peak Tms are very close so when co-amplifying a small broad peak results. Although two distinct peaks are the preferred result, this broad peak is a unique signature of the presence of both these HPV types.

Overall Multiplex Results

Current technologies suggest that four different amplicons per channel could be melted in the range of 68 to 83° C. to yield a total of 16 melts in a four channel system or 20 melts in a five channel system.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of detecting the presence or absence of a target nucleic acid variant in a sample, wherein a target nucleic acid may occur in at least two variants, the method comprising
(a) providing at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;
(b) providing at least one soluble light emission modifier, which, when the modifier non-covalently binds double stranded DNA incorporating the labeled oligonucleotide, alters light emission from the first label compared to light emission of the first label in the presence of the soluble light emission modifier when the labeled oligonucleotide is single-stranded;

(c) amplifying the target nucleic acid in the sample in the presence of the labeled oligonucleotide and the soluble light emission modifier in an amplification reaction under the selected condition such that the labeled oligonucleotide is extended to produce a first double-stranded labeled amplicon incorporating the labeled oligonucleotide, wherein the first double-stranded labeled amplicon has a different melting temperature depending on which of the at least two target nucleic acid variants are amplified;

(d) detecting the melting temperature of the double-stranded labeled amplicon into two strands by monitoring the signal of the label under changing temperature; and (e) correlating the melting temperature of the double-stranded labeled amplicon to the presence of one of the at least two target variants, thereby detecting the presence or absence of a target nucleic acid variant in a sample.

2. The method of claim 1, further comprising
providing a second labeled oligonucleotide comprising a second label, which second label comprises at least one light emitting moiety and wherein at least a subsequence of the second labeled oligonucleotide is sufficiently complementary to at least a second subsequence of the target nucleic acid that may occur in at least two variants such that the second labeled oligonucleotide hybridizes with the second target nucleic acid under the selected condition, and wherein signal from the second label can be distinguished from the signal of the first label,
wherein the at least one soluble light emission modifier, when intercalated in double stranded DNA incorporating the second labeled oligonucleotide alters light emission from the second label compared to light emission of the second label when the second labeled oligonucleotide is single-stranded in the presence of the soluble light emission modifier;
wherein the sample comprises at least one variant of the target nucleic acid and the amplifying step (c) further comprises amplifying the nucleic acid in the sample in the presence of the second labeled oligonucleotide in the amplification reaction such that the second labeled oligonucleotide is extended to produce a second labeled amplicon incorporating the second labeled oligonucleotide, and wherein the second labeled amplicon has a different melting temperature depending on which of the at least two target nucleic acid variants are amplified;
wherein the detecting step (d) further comprises detecting the melting temperature of the second labeled amplicon by monitoring the signal of the second label under changing temperature; and
wherein the correlating step (e) further comprises correlating the melting temperature of the second labeled amplicon to the presence of a second target nucleic acid variant.

3. The method of claim 2, wherein the second labeled amplicon comprises different target nucleic acid variant sequences compared to the first labeled amplicon.

4. The method of claim 1, wherein the modifier is a diazine dye or a thiazine dye.

5. The method of claim 1, wherein the modifier is selected from the group consisting of an azocarmine dye, a phenazine dye, an oxazine dye, diethylsafraninazodimethylaniline chloride, methylene blue, methylene green, thionin, 1,9-dimethylmethylene blue, sym-dimethylthionin, toluidine blue O, new methylene blue, methylene violet bernthsen, azure A, azure B, and azure C.

6. The method of claim 1, wherein the first label comprises a fluorescent dye.

7. The method of claim 1, wherein the first label is selected from the group consisting of a rhodamine dye, flourescein dye, and a cyanine dye.

8. The method of claim 2, wherein the second label is selected from the group consisting of a rhodamine dye, flourescein dye, and a cyanine dye.

9. The method of claim 1, wherein the target nucleic acid is a human, animal, oncogene, viral, or bacterial nucleic acid.

10. The method of claim 1, wherein the target nucleic acid is a viral nucleic acid.

11. The method of claim 1, wherein the melting temperatures of the amplicons of the at least two variants differ by at least 5 degrees C.

12. A method of detecting the presence or absence of a target nucleic acid variant in a sample, wherein a target nucleic acid may occur in at least two variants, the method comprising (a) providing at least one labeled oligonucleotide comprising a first label, which first label comprises at least one light emitting moiety and wherein at least a subsequence of the labeled oligonucleotide is sufficiently complementary to at least a subsequence of the target nucleic acid such that the labeled oligonucleotide hybridizes with the target nucleic acid under a selected condition;

(b) providing at least one soluble light emission modifier, which, when the modifier non-covalently binds double stranded DNA incorporating the labeled oligonucleotide, alters light emission from the first label compared to light emission of the first label in the presence of the soluble light emission modifier when the labeled oligonucleotide is single-stranded;

(c) amplifying the target nucleic acid in the sample in the presence of the labeled oligonucleotide and the soluble light emission modifier in an amplification reaction under the selected condition such that the labeled oligonucleotide is extended to produce a first double-stranded labeled amplicon incorporating the labeled oligonucleotide, wherein the first double-stranded labeled amplicon has a different melting temperature depending on which of the at least two target nucleic acid variants are amplified;

(d) detecting the melting temperature of the double-stranded labeled amplicon across the amplicon's full length into two strands by monitoring the signal of the label under changing temperature; and (e) correlating the melting temperature of the double-stranded labeled amplicon to the presence of one of the at least two target variants, thereby detecting the presence or absence of a target nucleic acid variant in a sample.

* * * * *